United States Patent
Nomura et al.

(10) Patent No.: US 9,572,341 B2
(45) Date of Patent: Feb. 21, 2017

(54) METHOD FOR ENHANCING EFFICACY OF AGRICHEMICAL, AND AGRICHEMICAL-CONTAINING COMPOSITION

(71) Applicant: KAO CORPORATION, Tokyo (JP)

(72) Inventors: Takayuki Nomura, Wakayama (JP); Masatoshi Kamei, Wakayama (JP); Kazuhiko Kurita, Wakayama (JP); Hiromoto Mizushima, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/845,547

(22) Filed: Sep. 4, 2015

(65) Prior Publication Data

US 2015/0373969 A1    Dec. 31, 2015

Related U.S. Application Data

(63) Continuation of application No. 13/257,337, filed as application No. PCT/JP2010/054926 on Mar. 23, 2010, now Pat. No. 9,161,530.

(30) Foreign Application Priority Data

Mar. 30, 2009   (JP) .................. 2009-082291

(51) Int. Cl.
| | | |
|---|---|---|
| *A01N 25/24* | (2006.01) | |
| *A01N 55/00* | (2006.01) | |
| *A01N 25/04* | (2006.01) | |
| *A01N 31/14* | (2006.01) | |
| *A01N 47/38* | (2006.01) | |
| *A01N 55/04* | (2006.01) | |
| *A01N 57/14* | (2006.01) | |
| *A01N 57/20* | (2006.01) | |

(52) U.S. Cl.
CPC .............. *A01N 25/24* (2013.01); *A01N 25/04* (2013.01); *A01N 55/00* (2013.01)

(58) Field of Classification Search
CPC ......... A01N 25/24; A01N 25/04; A01N 55/00
See application file for complete search history.

(56) References Cited

U.S. PATENT DOCUMENTS

| | | | |
|---|---|---|---|
| 3,899,439 A | * | 8/1975 | Mahlman ................ C08L 1/284 106/190.1 |
| 4,762,718 A | | 8/1988 | Marks, Sr. |
| 5,096,711 A | | 3/1992 | Dookhith et al. |
| 5,626,858 A | * | 5/1997 | Narayanan ............ A01N 25/10 424/405 |
| 5,674,514 A | | 10/1997 | Hasslin |
| 5,908,708 A | * | 6/1999 | Sekutowski ............. A01G 7/00 427/384 |
| 2003/0050194 A1 | | 3/2003 | Hopkinson et al. |
| 2003/0152631 A1 | | 8/2003 | Morishima et al. |
| 2007/0041866 A1 | | 2/2007 | Miyata et al. |
| 2007/0065388 A1 | | 3/2007 | Miyamoto et al. |
| 2007/0066486 A1 | | 3/2007 | Kawanaka et al. |

FOREIGN PATENT DOCUMENTS

| | | |
|---|---|---|
| CN | 1114855 A | 1/1996 |
| CN | 101530079 A | 9/2009 |
| EP | 0143297 A1 | 6/1985 |
| EP | 0 760 207 A1 | 3/1997 |
| GB | 2 040 684 A | 9/1980 |
| JP | 61-243007 A | 10/1986 |
| JP | 1-186801 A | 7/1989 |
| JP | 1-268605 A | 10/1989 |
| JP | 1-305043 A | 12/1989 |
| JP | 7-112904 A | 5/1995 |
| JP | 10-306001 A | 11/1998 |
| JP | 2002-80314 A | 3/2002 |
| JP | 2002-167301 A | 6/2002 |
| JP | 2003-119428 A | 4/2003 |
| JP | 2003-286104 A | 10/2003 |
| JP | 2003-313101 A | 11/2003 |
| JP | 2005-289959 A | 10/2005 |
| JP | 2006-160702 A | 6/2006 |
| JP | 2007-84479 A | 4/2007 |
| JP | 2007-277215 A | 10/2007 |
| WO | WO 95/17817 A1 | 7/1995 |
| WO | WO 95/31903 A1 | 11/1995 |

OTHER PUBLICATIONS

LookChem (http://www.lookchem.com/cas-900/9004-64-2.html, hydroxypropyl cellulose, 2014).*
A full machine translation of JP-10-306001-A dated Nov. 17, 1998.
A full machine translation of JP-1-186801-A dated Jul. 26, 1989.
A full machine translation of JP-1-305043-A dated Dec. 8, 1989.
A full machine translation of JP-2002-167301-A dated Jun. 11, 2002.
A full machine translation of JP-2003-119428-A date Apr. 23, 2003.
A full machine translation of JP-2003-286104-A dated Oct. 7, 2003.
A full machine translation of JP-2003-313101-A dated Nov. 6, 2003.
A full machine translation of JP-2006-160702-A dated Jun. 22, 2006.

(Continued)

*Primary Examiner* — Mark V Stevens
(74) *Attorney, Agent, or Firm* — Birch, Stewart, Kolasch & Birch, LLP

(57) ABSTRACT

An agrichemical-containing composition that exhibits excellent agrichemical efficacy is provided. The agrichemical-containing composition comprises hydroxypropyl cellulose, an agrichemical, an organic solvent having a saturated vapor pressure of 50 mmHg or higher at 25° C., and water. When the composition as a whole is taken as 100 wt %, the content of the organic solvent is 0.02 to 1 wt %, and the weight ratio of the hydroxypropyl cellulose to the organic solvent (hydroxypropyl cellulose/organic solvent) is in a range of 0.1 to 2.

5 Claims, No Drawings

(56) References Cited

A full machine translation of JP-61-243007-A dated Oct. 29, 1986.
A full machine translation of JP-7-112904-A dated May 2, 1995.
Extended European Search Report, dated Jan. 27, 2014, for European Application No. 10758466.6.
Gottlieb et al., "NMR Chemical Shifts of Common Laboratory Solvents as Trace Impurities," Journal of Organic Chemistry, vol. 62, 1997, pp. 7512-7515.
International Search Report, dated Apr. 27, 2010, issued in PCT/JP2010/054926.

* cited by examiner

METHOD FOR ENHANCING EFFICACY OF AGRICHEMICAL, AND AGRICHEMICAL-CONTAINING COMPOSITION

CROSS-REFERENCE TO RELATED APPLICATIONS

This application is a Continuation of co-pending application Ser. No. 13/257,337 filed on Sep. 19, 2011, which is a National Phase of PCT International Application No. PCT/JP2010/054926 filed on Mar. 23, 2010, which claims priority under 35 U.S.C. §119(a) to Patent Application No. 2009-082291 filed in Japan on Mar. 30, 2009. All of the above applications are hereby expressly incorporated by reference into the present application.

TECHNICAL FIELD

The present invention relates to a method for enhancing the efficacy of an agrichemical and an agrichemical-containing composition.

BACKGROUND ART

Agrichemicals including insecticides, fungicides, herbicides, miticides, and plant growth regulators are used in such forms as an emulsion, a wettable powder, granules, a dusting powder, flowables, and a solution. At that time, a variety of contrivances are made in terms of the physical properties of the formulations in order to exploit the effects of the agrichemicals to a sufficient degree.

Conventionally, a variety of surfactants have been used in agrichemical-containing compositions to exploit the effects of the agrichemicals to a sufficient degree. For example, it is known that an agrichemical-containing composition that exerts a strong effect on bipyridinium-based herbicides can be achieved by combining an anionic surfactant and a chelating agent (see Patent Document 1, for example). Further, it is also known that a highly-effective agrichemical-containing composition can be achieved by mixing a chelating agent with a cationic surfactant and further adding a different surfactant to the mixture (see Patent Document 2, for example).

Further, the use of amine oxide in agrichemical-containing compositions is also known (see Patent Document 3, for example).

Further, a water continuous phase in which N-(phosphonomethyl)glycine salt is dissolved has been used to provide a hardly water-soluble agrichemical active ingredient that is in a solid-state at room temperature with storage stableness and to enhance the efficacy of the ingredient (see Patent Document 4, for example).

PRIOR ART DOCUMENT

Patent Document

Patent Document 1: WO 95/31903 A1
Patent Document 2: WO 95/17817 A1
Patent Document 3: JP H1-268605 A
Patent Document 4: JP 2007-277215 A

DISCLOSURE OF INVENTION

Problem to be Solved by the Invention

However, in recent years, a far superior agrichemical-containing composition is desired as the demands of the market grow.

It is an object of the present invention to provide a method for enhancing the efficacy of an agrichemical and an agrichemical-containing composition.

Means for Solving Problem

The present inventors have found that a combination of a specific cellulose derivative, a specific organic solvent, and an agrichemical is effective in improving the efficacy of the agrichemical, thus completing the present invention.

The present invention is directed to a method for enhancing the efficacy of an agrichemical by using a composition comprising hydroxypropyl cellulose, an organic solvent having a saturated vapor pressure of 50 mmHg or higher at 25° C., and water. When a total of the composition and the agrichemical is taken as 100 wt %, the content of the organic solvent is 0.02 to 1 wt %, and the weight ratio of the hydroxypropyl cellulose to the organic solvent (hydroxypropyl cellulose/organic solvent) is in a range of 0.1 to 2.

Further, the present invention is directed to an agrichemical-containing composition comprising hydroxypropyl cellulose, an agrichemical, an organic solvent having a saturated vapor pressure of 50 mmHg or higher at 25° C., and water. When the composition as a whole is taken as 100 wt %, the content of the organic solvent is 0.02 to 1 wt %, and the weight ratio of the hydroxypropyl cellulose to the organic solvent (hydroxypropyl cellulose/organic solvent) is in a range of 0.1 to 2.

Further, the present invention is directed to a method for improving the quality of a plant. The method includes applying the agrichemical-containing composition of the present invention to the plant.

Effects of the Invention

According to the present invention, it is possible to enhance the efficacy of an agrichemical.

DESCRIPTION OF THE INVENTION

Although the mechanism of the present invention is not clear, the following can be considered as one possible mechanism. When a specific organic solvent, more specifically, an organic solvent having a saturated vapor pressure of 50 mmHg or higher at 25° C. is selected as a solvent for a composition comprising an agrichemical, the rate at which the solvent evaporates from the composition when the composition is applied to a plant becomes faster than the case of using water as the only solvent. As a result, the viscosity of the composition using such a specific organic solvent increases promptly on the surface of the plant to which the composition is applied, so that the agrichemical can easily adhere onto the surface of the plant. Further, when hydroxypropyl cellulose is contained in a composition comprising an agrichemical, the hydroxypropyl cellulose exhibits its surface activation capability and coating forming capability, whereby facilitating the formation of a film containing the agrichemical on the surface of a plant to which the composition is applied. Thus, the agrichemical can easily adhere onto the surface of the plant. It is conceivable that, as a result of the combination of these effects, the method for enhancing the efficacy of an agrichemical and the agrichemical-containing composition of the present invention improve the efficacy of an agrichemical.

[Hydroxypropyl Cellulose]

The hydroxypropyl cellulose is represented by the following formula.

[CHEMICAL FORMULA 1]

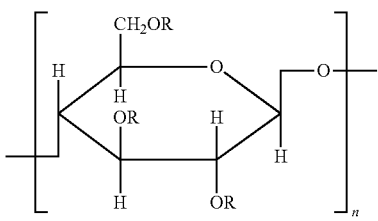
(I)

Where R=H or —(CH$_2$CH(CH$_3$)—O)$_m$H (where m is 0 or an integer of 1 to 5. Note that all of Rs in the formula (I) do not have m=0 at the same time.)

The degree of polymerization (n) of the hydroxypropyl cellulose is, for example, 30 to 1,500. In terms of enhancing the efficacy of an agrichemical, the degree of polymerization of the hydroxypropyl cellulose is preferably 40 to 1,200, and more preferably 70 to 500. Further, the viscosity of the hydroxypropyl cellulose measured at a 2 wt % concentration at 20° C. is, for example, 1.0 to 10,000 mPa·s. In terms of improving the enhancement of an agrichemical, the viscosity is preferably 2.0 to 4,000 mPa·s, and more preferably 3.0 to 1,000 mPa·s. Note that the hydroxypropyl cellulose can be produced by known methods from the documents or a commercially available product may be used.

[Agrichemical]

It is possible to use a known agrichemical as the agrichemical used in the method for enhancing the efficacy of an agrichemical and the agrichemical-containing composition of the present invention. An agrichemical selected from the group consisting of (B1) fungicides, (B2) insecticides, (B3) miticides, and (B4) herbicides selected from glyphosate and bialaphos agents is preferred, and examples of which include those listed in "Agriculture Handbook 1998 version" (Tenth edition, Dec. 15, 1998, published by the Japan Plant Protection Association).

Examples of (B1) fungicides include: organic sulfur fungicides such as a zineb agent, a maneb agent, a thiuram agent, a mancozeb agent, a polycarbamate agent, and a propineb agent; benzimidazole-based fungicides such as a benomyl agent and a thiophanate-methyl agent; dicarboxylic acid-based fungicides such as an iprodione agent and a procymidone agent, other synthetic fungicides such as a triazine agent, an iminoctadine triacetate agent, an isoprothiolane agent, a TPN agent, a probenazole agent, a captan agent, a fluorimide agent, a DPC agent, an iminoctadine albesilate agent; sterol biosynthesis inhibitors such as a triflumizole agent, a bitertanol agent, a pyrifenox agent, a fenarimol agent, a triforine agent, a triadimefon agent, a myclobutanil agent, a difenoconazole agent, an imibenconazole agent; acid amide-based fungicides such as a metalaxyl agent and a mepronil agent; copper fungicides such as an inorganic copper agent and an organic copper agent; antibiotic fungicides such as a streptomycin agent, a polyoxin agent, a blasticidin S agent, a kasugamycin agent, validamycin, and an oxytetracycline agent; soil fungicides such as an echlomezol agent and a hymexazol agent; melamine biosynthesis inhibitors such as a fthalide agent and a carpropamid agent; organophosporus fungicides such as an IBP agent, an EDDP agent and a fosethyl agent; inorganic fungicides such as an inorganic sulfur agent and a hydrogen carbonate agent; methoxyacrylate-based fungicides such as azoxystrobin and kresoxim-methyl agents; anilinopyrimidine-based fungicides such as a mepanipyrim agent; synthetic antibacterial agents such as an oxolinic acid agent; natural product fungicides such as soybean lecithin agent; and fungicides of biological origin such as an antagonistic antibacterial agent.

Examples of (B2) insecticides include: pyrethroid-based insecticides such as a fenvalerate agent, a cyfluthrin agent, a permethrin agent, a flucythrinate, and an ethofenprox agent; organophosphorous insecticides such as a DDVP agent, a MEP agent, a malathon agent, a dimethoate agent, a PAP agent, a MPP agent, a DMTP agent, and an EPN agent; carbamate-based insecticides such as a BPMC agent, a NAC agent, and a methomyl agent; nereistoxin-based insecticides such as a cartap agent; natural product-based insecticides such as a pyrethrin agent derived from pyrethrum, a piperonylbutoxide agent, a rotenone agent derived from derris as a leguminous shrub, a nicotine agent, a soybean lecithin agent, and a starch agent. Examples of insect growth regulators (IGR) include a diflubenzuron agent, a teflubenzuron agent, a chlorfluazuron agent, a buprofezin agent, an isoprothiolane agent, and a flufenoxuron agent.

Examples of (B3) miticides include a Kelthane agent, a BPPS agent, a fenbutatin oxide agent, a hexythiazox agent, an amitraz agent, a fenpyroximate agent, a tebufenpyrad agent, a halfenprox agent, a bialaphos agent, chloronicotinyl-based insecticides such as an imidacloprid agent, other synthetic insecticides such as a sodium oleate agent and a potassium oleate agent, nematocides such as a D-D agent, a dazomet agent and a benomyl agent, and insecticides of biological origin such as a BT agent.

Examples of (B4) herbicides include: acid amide-based herbicides such as a DCPA agent, an alachlor agent, and an Asulam agent; urea-based herbicides such as a DCMU agent and a linuron agent; bipyridium-based herbicides such as a Paraquat agent and a diquat agent; diazine-based herbicides such as a bromacil agent and a lenacil agent; S-triazine-based herbicides such as a CAT agent and a simetryn agent; other organic herbicides such as nitrile-based herbicides, for example, a DBN agent, and a sethoxydim agent and a clethodim agent; dinitroaniline-based herbicides such as a trifluralin agent and a pendimethalin agent; carbamate-based herbicides such as a thiobencarb agent; aromatic carboxylic acid-based herbicides such as a MDBA agent; phenoxy acid-based herbicides such as a 2,4-PA agent and a cyhalofop-butyl agent; organophosphorous herbicides such as a piperophos agent and a butamifos agent; amino acid-based herbicides such as glyphosate agents, for example, ammonium=N-(phosphonomethyl)glycinate available as glyphosate, isopropylammonium=N-(phosphonomethyl) glycinate available as Roundup, trimethylsulfonium=N-(phosphonomethyl)glycinate available as Touchdown, and sodium=N-(phosphonomethyl)glycinate available as Impulse, bialaphos agents, for example, L-2-amine-4-[(hydroxy)(methyl)phosphinoyl]-butyryl-L-alanyl-L-alanine available as Herbiace; fatty acid-based herbicides such as a pelargonic acid agent and a DPA agent; sulfonylurea-based herbicides such as a thifensulfuron methyl agent, a flazasulfuron agent and a bensulfuron methyl agent; pyrimidyloxy benzoic acid-based herbicides such as a bispyribac-sodium salt; and diazole-based herbicides such as a pyrazolate agent.

Among these herbicides, acid amide-based herbicides, diazine-based herbicides, nitrile-based herbicides, dinitroaniline-based herbicides, aromatic carboxylic acid-based herbicides, and amino acid-based herbicides are preferable in terms of enhancing the efficacy of the agrichemical, i.e., the herbicidal potency.

When the composition as a whole is taken as 100 wt %, the content of the agrichemical is preferably 0.02 to 1 wt %, more preferably 0.03 to 1 wt %, and still more preferably 0.04 to 1 wt % in terms of enhancing the efficacy of the agrichemical.

[Organic Solvent]

As described above, the organic solvent is an organic solvent having a saturated vapor pressure of 50 mmHg or higher at 25° C. The saturated vapor pressure of the organic solvent refers to a gas pressure at the time a liquid and gas as pure substances of the organic solvent are in equilibrium. The saturated vapor pressure can be measured by a direct method with a U-shaped mercury manometer. As a result of using such an organic solvent, the rate at which the solvent evaporates from the composition when the composition is applied to a plant becomes faster than the case of using water as the only solvent. Consequently, the viscosity of the composition using such a specific organic solvent increases promptly on the surface of the plant to which the composition is applied, so that the agrichemical can easily adhere onto the surface of the plant. Examples of organic solvents having a saturated vapor pressure of 50 mmHg or higher at 25° C. include ethanol (59 mmHg), trifluoroethanol (75 mmHg), dichloroethane (83 mmHg), acetonitrile (88 mmHg), methyl ethyl ketone (91 mmHg), ethyl acetate (95 mmHg), cyclohexane (98 mmHg), trifluoroacetate (108 mmHg), methanol (127 mmHg), diisopropyl ether (149 mmHg), tetrahydrofuran (162 mmHg), chloroform (195 mmHg), acetone (231 mmHg), dichloromethane (436 mmHg), and diethyl ether (537 mmHg), and among which methanol, ethanol, acetone, methyl ethyl ketone, and ethyl acetate are preferable (each value in parenthesis indicates the saturated vapor pressure of the solvent at 25° C.). Further, in terms of enhancing the efficacy of the agrichemical, it is preferable to use an organic solvent having a saturated vapor pressure of 55 mHg or higher, more preferably 70 mmHg or higher, still preferably 90 mmHg or higher, and still more preferably 100 mmHg or higher at 25° C.

When the composition as a whole is taken as 100 wt %, the content of the organic solvent is 0.02 to 1 wt %. In terms of enhancing the efficacy of the agrichemical, the content of the organic solvent is preferably 0.03 to 1 wt %, more preferably 0.03 to 0.8 wt %, and still more preferably 0.03 to 0.1 wt %.

In terms of the stability of the agrichemical-containing composition as well as achieving the adhesion of the agrichemical by evaporation of the solvent and the coating formation due to the hydroxypropyl cellulose, the weight ratio of the hydroxypropyl cellulose to the organic solvent (hydroxypropyl cellulose/organic solvent) in the agrichemical-containing composition of the present invention is in a range of 0.1 to 2. In terms of enhancing the agrichemical efficacy, the weight ratio of the hydroxypropyl cellulose to the organic solvent is in a range of preferably 0.2 to 1.7, and more preferably 0.5 to 1.0. Further, in the composition comprising hydroxypropyl cellulose, an organic solvent having a saturated vapor pressure of 50 mmHg or higher at 25° C., and water to be used in the method for enhancing the efficacy of an agrichemical, the weight ratio of the hydroxypropyl cellulose to the organic solvent (hydroxypropyl cellulose/organic solvent) is in a range of 0.1 to 2 in terms of the stability of the agrichemical-containing composition as well as achieving the adhesion of the agrichemical by evaporation of the solvent and the coating formation due to the hydroxypropyl cellulose. In terms of enhancing the agrichemical efficacy, the weight ratio of the hydroxypropyl cellulose to the organic solvent is in a range of preferably 0.2 to 1.7, and more preferably 0.5 to 1.0.

<Water>

The agrichemical-containing composition of the present invention contains water. When the composition as a whole is taken as 100 wt %, the content of the water is preferably 95 wt % or more, more preferably 97 wt % or more, and still more preferably 98 wt % or more in terms of enhancing the agrichemical efficacy. Further, in the method for enhancing the efficacy of an agrichemical of the present invention, when a total of the composition and the agrichemical is taken as 100 wt %, the content of the water is preferably 95 wt % or more, more preferably 97 wt % or more, and still more preferably 98 wt % or more in terms of enhancing the agrichemical efficacy.

[Other Additives]

The agrichemical-containing composition of the present invention may further contain surfactants, chelating agents, pH adjusters, inorganic salts, thickeners, plant growth regulators, fertilizers, preservatives, and the like. Further, the composition comprising hydroxypropyl cellulose, an organic solvent having a saturated vapor pressure of 50 mmHg or higher at 25° C., and water to be used in the method for enhancing the efficacy of an agrichemical of the present invention may further contain surfactants, chelating agents, pH adjusters, inorganic salts, thickeners, plant growth regulators, fertilizers, preservatives, and the like.

<Surfactant>

When a surfactant is further used in conjunction with the hydroxypropyl cellulose in the agrichemical-containing composition of the present invention, it is possible to reduce the amount of the hydroxypropyl cellulose used in the composition while maintaining the hydroxypropyl cellulose's effect of enhancing the efficacy of the agrichemical. A nonionic surfactant, an anionic surfactant, a cationic surfactant, an amphoteric surfactant, or a mixture thereof can be used as the surfactant. Further, when a surfactant is further used in the composition comprising hydroxypropyl cellulose, an organic solvent having a saturated vapor pressure of 50 mmHg or higher at 25° C., and water to be used in the method for enhancing the efficacy of an agrichemical of the present invention, it is possible to reduce the amount of the hydroxypropyl cellulose used in the composition while maintaining the hydroxypropyl cellulose's effect of enhancing the efficacy of the agrichemical. A nonionic surfactant, an anionic surfactant, a cationic surfactant, an amphoteric surfactant, or a mixture thereof can be used as the surfactant.

Examples of nonionic surfactants include polyoxyalkylene alkyl ethers such as polyoxyethylene alkyl ethers (e.g., polyoxyethylene coleyl ether), polyoxyalkylene alkyl aryl ethers such as polyoxyethylene alkyl phenol, a polyoxyalkylene alkyl aryl ether/formaldehyde condensate, polyoxyalkylene aryl ether, polyoxyalkylene alkyl ester, polyoxyalkylene alkyl sorbitol ester, polyoxyalkylene sorbitan ester, polyoxyalkylene alkyl glycerol ester, polyoxyalkylene block copolymers (e.g., those containing a polyoxypropylene group), polyoxyalkylene block copolymer alkyl glycerol ester, polyoxyalkylene alkyl sulfonamide, polyoxyalkylene rosin ester, alkyl glycoside, alkyl polyglycoside, polyoxyalkylene alkyl polyglycoside, and mixtures of two or more of these.

Examples of cationic surfactants include monoalkyl di-lower alkylamine, dialkyl mono-lower alkylamine, an alkylamine ethylene oxide adduct, an alkylamine propylene oxide adduct, e.g., a tallow amine ethylene oxide adduct, an coleyl amine ethylene oxide adduct, a soy amine ethylene oxide adduct, a coco amine ethylene oxide adduct, a synthetic alkylamine ethylene oxide adduct, an octyl amine ethylene oxide adduct, and quaternary derivatives thereof (e.g., those quaternarized with methyl chloride, dimethylsulfuric acid, diethylsulfuric acid, benzyl chloride, etc.), and mixtures thereof.

Typical anionic surfactants are available in the form of an aqueous solution or in a solid state, and examples of such anionic surfactants include mono- and di-alkyl naphthalene sodium sulfonate, sodium α-olefinsulfonate, sodium alkanesulfonate, alkylsulfosuccinate, alkylsulfate, polyoxyalkylene alkyl ether sulfate, polyoxyalkylene alkyl aryl ether sulfate, polyoxyalkylene styryl phenyl ether sulfate, mono- and di-alkylbenzene sulfonate, alkyl naphthalene sulfonate, alkyl naphthalene sulfonate-formaldehyde condensates, alkyldiphenyl ether sulfonate, olefinic sulfonate, mono- and di-alkylphosphate, polyoxyalkylene mono- and di-alkylphosphate, polyoxyalkylene mono- and di-phenyl ether phosphate, polyoxyalkylene mono- and di-alkyl phenyl ether phosphate, polycarboxylate, linear and branched alkylamide polyoxyalkylene ether carboxylic acid or salts thereof, alkyl polyoxyalkylene ether carboxylates, alkenyl polyoxyalkylene ether carboxylates, aliphatic acids or salts thereof, e.g., capric acid and salts thereof, lauric acid and salts thereof, stearic acid and salts thereof, oleic acid and salts thereof, N-methyl fatty acid taurides, and mixtures of two or more of these (including salts such as sodium, potassium, ammonium and amine salts).

Examples of suitable amphoteric surfactants include Armox C/12, Monaterics, Miranols, betaine, Lonzaines, and mixtures thereof.

Among these surfactants, nonionic surfactants, in particular, polyoxyalkylene alkyl ethers (particularly polyoxyethylene alkyl ether) and polyoxyalkylene sorbitan esters (particularly polyoxyethylene sorbitan ester) are particularly preferable in terms of enhancing the efficacy of the agrichemical.

When a surfactant is further contained in the composition of the present invention, it is preferable to use the surfactant in conjunction with the hydroxypropyl cellulose at a weight ratio (hydroxypropyl cellulose/surfactant) in a range of 0.01 to 50, more preferably 0.1 to 50, still preferably 0.1 to 30, and still more preferably 0.2 to 10 in terms of enhancing the efficacy of the agrichemical. When a surfactant is further contained in the composition comprising hydroxypropyl cellulose, an organic solvent having a saturated vapor pressure of 50 mmHg or higher at 25° C. and water to be used in the method for enhancing the efficacy of an agrichemical of the present invention, it is preferable to use the surfactant in conjunction with the hydroxypropyl cellulose at a weight ratio (hydroxypropyl cellulose/surfactant) in a range of 0.01 to 50, more preferably 0.1 to 50, still preferably 0.1 to 30, and still more preferably 0.2 to 10 in terms of enhancing the efficacy of the agrichemical.

<Chelating Agent>

In terms of enhancing the efficacy of the agrichemical, a chelating agent may be further contained in the agrichemical-containing composition of the present invention. The chelating agent is not particularly limited as long as it has an ability to chelate metal ions. Further, a chelating agent may be further contained in the composition comprising hydroxypropyl cellulose, an organic solvent having a saturated vapor pressure of 50 mmHg or higher at 25° C., and water to be used in the method for enhancing the efficacy of an agrichemical of the present invention in terms of enhancing the efficacy of the agrichemical. Examples of chelating agents that can be used in the present invention include aminopolycarboxylic acid-based chelating agents, aromatic and aliphatic carboxylic acid-based chelating agents, amino acid-based chelating agents, ether polycarboxylic acid-based chelating agents, phosphonic acid-based chelating agents such as iminodimethyl phosphonic acid (IDP) and alkyldiphosphonic acid (ADPA), hydroxycarboxylic acid-based chelating agents, phosphoric acid-based chelating agents, polymeric electrolyte (including an oligomer electrolyte) based chelating agents, and dimethyl glyoxime (DG). These chelating agents may be in the form of a free acid or in the form of salt such as sodium salt, potassium salt, or ammonium salt. Alternatively, they may be hydrolysable ester derivatives thereof.

Specific examples of aminopolycarboxylic acid-based chelating agents include the following:

a) compounds represented by the chemical formula $RNY_2$ b) compounds represented by the chemical formula $NY_3$ c) compounds represented by the chemical formula R—NY—CH$_2$CH$_2$—NY—R d) compounds represented by the chemical formula R—NY—CH$_2$CH$_2$—NY$_2$ e) compounds represented by the chemical formula Y$_2$N—R'—NY$_2$, and f) compounds analogous to the compounds of e) and having 4 or more Y groups, for example,

[CHEMICAL FORMULA 2]

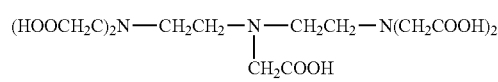

compounds represented by the chemical formula 2.

Where Y represents —CH$_2$COOH or —CH$_2$CH$_2$COOH, R represents a group constituting a known chelating agent, such as a hydrogen atom, an alkyl group, a hydroxyl group or a hydroxyalkyl group, and R' represents a group constituting a known chelating agent, such as an alkylene group or a cycloalkylene group.

Typical examples of aminopolycarboxylic acid-based chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl) iminodiacetic acid (HIMDA), diethylenetriaminepentaacetic acid (DTPA), N-(2-hydroxyethyl) ethylenediaminetriacetic acid (EDTA-OH), and glycol ether diaminetetraacetic acid (GEDTA), as well as salts thereof.

Examples of aromatic and aliphatic carboxylic acid-based chelating agents include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranilic acid), phthalic acid, trimellitic acid and gallic acid, as well as salts, methyl esters and ethyl esters thereof. Examples of amino acid-based chelating agents include glycine, serine, alanine, lysine, cystine, cysteine, ethionine, tyrosine, methionine, and salts and derivatives thereof.

Furthermore, examples of ether polycarboxylic acid-based chelating agents include diglycolic acid, compounds represented by the following formula, analogous compounds thereof and salts thereof (e.g., sodium salts).

[CHEMICAL FORMULA 3]

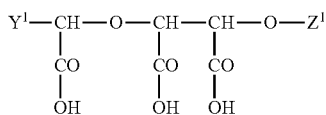

Where $Y^1$ represents a hydrogen atom, —$CH_2COOH$ or —COOH, and $Z^1$ represents a hydrogen atom, —$CH_2COOH$ or

[CHEMICAL FORMULA 4]

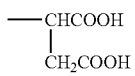

the above chemical formula.

Examples of hydroxycarboxylic acid-based chelating agents include malic acid, citric acid, glycolic acid, gluconic acid, heptonic acid, tartaric acid, lactic acid, and salts thereof.

Examples of phosphoric acid-based chelating agents include orthophosphoric acid, pyrophosphoric acid, triphosphoric acid, and polyphosphoric acid.

Examples of polymeric electrolyte (including an olygomer electrolyte) based chelating agents include an acrylate polymer, a maleic anhydride polymer, an α-hydroxyacrylate polymer, an itaconate polymer, and a copolymer composed of two or more of the monomers constituting these polymers, and an epoxysuccinate polymer.

In addition, ascorbic acid, thioglycolic acid, phytic acid, glyoxylic acid, and glyoxalic acid, as well as salts thereof can also be used suitably as a chelating agent in the present invention.

When a chelating agent is further contained in the composition of the present invention, it is preferable that the chelating agent is mixed with the composition in the proportion of 1 mol hydroxypropyl cellulose (total volume) to 0.05 to 15 mol chelating agent in terms of enhancing the efficacy of the agrichemical. Further, when a chelating agent is further contained in the composition comprising hydroxypropyl cellulose, an organic solvent having a saturated vapor pressure of 50 mmHg or higher at 25° C. and water to be used in the method for enhancing the efficacy of an agrichemical, it is preferable that the chelating agent is mixed with the composition in the proportion of 1 mol hydroxypropyl cellulose (total volume) to 0.05 to 15 mol chelating agent in terms of enhancing the efficacy of the agrichemical.

<pH Adjuster>

A known pH adjuster can be used in the present invention.

When a pH adjuster is further contained in the composition of the present invention, the weight ratio of the hydroxypropyl cellulose to the pH adjuster, i.e., the hydroxypropyl cellulose/the pH adjuster, is in a range of preferably 0.01 to 50, more preferably 0.1 to 50, still preferably 0.1 to 30, and still more preferably 0.2 to 10 in terms of enhancing the efficacy of the agrichemical. Further, when a pH adjuster is further contained in the composition comprising hydroxypropyl cellulose, an organic solvent having a saturated vapor pressure of 50 mmHg or higher at 25° C. and water to be used in the method for enhancing the efficacy of an agrichemical of the present invention, the weight ratio of the hydroxypropyl cellulose to the pH adjuster, i.e., the hydroxypropyl cellulose/the pH adjuster, is in a range of preferably 0.01 to 50, more preferably 0.1 to 50, still preferably 0.1 to 30, and still more preferably 0.2 to 10 in terms of enhancing the efficacy of the agrichemical.

<Inorganic Salts>

Examples of inorganic salts that can be used in the present invention include: inorganic mineral salts such as inorganic salt clay, talc, bentonite, zeolite, calcium carbonate, diaton earth, and white carbon; inorganic ammonium salts such as ammonium sulfate, ammonium nitrate, ammonium phosphate, ammonium thiocyanate, ammonium chloride, and ammonium sulfamate.

When inorganic salts are further contained in the composition of the present invention, the weight ratio of the hydroxypropyl cellulose to the inorganic salts, i.e., the hydroxypropyl cellulose/the inorganic salts, is in a range of preferably 0.01 to 50, more preferably 0.1 to 50, still preferably 0.1 to 30, and still more preferably 0.2 to 10 in terms of enhancing the efficacy of the agrichemical. Further, when inorganic salts are further contained in the composition comprising hydroxypropyl cellulose, an organic solvent having a saturated vapor pressure of 50 mmHg or higher at 25° C., and water to be used in the method for enhancing the efficacy of an agrichemical of the present invention, the weight ratio of the hydroxypropyl cellulose to the inorganic salts, i.e., the hydroxypropyl cellulose/the inorganic salts, is in a range of preferably 0.01 to 50, more preferably 0.1 to 50, still preferably 0.1 to 30, and still more preferably 0.2 to 10 in terms of enhancing the efficacy of the agrichemical.

<Plant Growth Regulator>

Moreover, examples of plant growth regulators include: auxin antagonists such as a hydrazide maleate agent and an uniconazole agent; auxin agents such as an indolebutyric acid agent, a 1-naphthyl acetamide agent and a 4-CPA agent; cytokinin agents such as a forchlorfenuron agent; gibberellin agents such as a gibberellin agent; other stunt agents such as a daminozide agent; antidesiccants such as a paraffin agent; other plant growth regulators such as a choline agent; plant growth regulators of biological origin such as a chlorella extract agent; and ethylene agents such as an ethephon agent.

When a plant growth regulator is further contained in the composition of the present invention, the weight ratio of the hydroxypropyl cellulose to the plant growth regulator, i.e., the hydroxypropyl cellulose/the plant growth regulator, is in a range of preferably 0.01 to 50, more preferably 0.1 to 50, still preferably 0.1 to 30, and still more preferably 0.2 to 10 in terms of enhancing the efficacy of the agrichemical. Further, when a plant growth regulator is further contained in the composition comprising hydroxypropyl cellulose, an organic solvent having a saturated vapor pressure of 50 mmHg or higher at 25° C. and water to be used in the method for enhancing the efficacy of an agrichemical of the present invention, the weight ratio of the hydroxypropyl cellulose to the plant growth regulator, i.e., the hydroxypropyl cellulose/the plant growth regulator, is in a range of preferably 0.01 to 50, more preferably 0.1 to 50, still preferably 0.1 to 30, and still more preferably 0.2 to 10 in terms of enhancing the efficacy of the agrichemical.

[Agrichemical-Containing Composition]

The form of the agrichemical-containing composition of the present invention is not limited and the composition can be in any form such as an emulsion, flowables, or a solution. For this reason, the composition may contain other additives, for example, an emulsifier, a disperser, a carrier, etc., in accordance with its form. The use of the agrichemical-containing composition according to the present invention provides the efficacy enhancing effect as an object of the present invention because the agrichemical-containing composition is used in the variety of forms as mentioned above.

[Method for Improving Quality of Plant]

As described above, the method for improving the quality of a plant of the present invention includes applying the agrichemical-containing composition to the plant. According to the method for improving the quality of a plant of the present invention, when the agrichemical is, for example, an herbicide, it is possible to improve the effect of the herbicide on plants in fields, fallow land, paddy furrows, orchards, meadowland, lawns, forests, and nonagricultural land. Further, according to the method for improving the quality of a plant of the present invention, when the agrichemical is, for example, an insecticide or fungicide, it is possible to improve the effect of the insecticide or fungicide on plants in fields, fallow land, paddy furrows, orchards, meadowland, lawns, forests, and nonagricultural land.

A variety of means can be used to supply the agrichemical-containing composition of the present invention to plants. For example, the agrichemical-containing composition of the present invention can be sprayed directly to leaves, stems, fruits, etc. of plants, and as in hydroponics or rock wool, the composition can be diluted and mixed with a hydroponic solution or supply water that is in contact with the roots to supply (apply) the composition to the root surface or the like. Because the agrichemical-containing composition of the present invention has a surprising effect of allowing the agrichemical to promptly adhere onto the surface of plants, it is preferable to spray the agrichemical-containing composition to the overground part of plants, and it is more preferable to spray the composition to the leaves as a way to supply the agrichemical-containing composition of the present invention. At that time, the plants can be directly immersed into a container containing the agrichemical-containing composition of the present invention.

Examples

Abbreviations used in Tables 3 to 6 for hydroxypropyl celluloses and organic solvents are as follows. The saturated vapor pressure of each organic solvent at 25° C. is also shown.

<Hydroxypropyl Celluloses>

TABLE 1

| Abbreviations in Tables | | Molecular weight | Degree of polymerization | 2% viscosity (mPa · s) |
| --- | --- | --- | --- | --- |
| HPC (1) | hydroxypropyl cellulose NISSO HPC-SSL (manufactured by Nippon Soda Co., Ltd.) | 15,000 to 30,000 | 42 to 84 | 2.0 to 2.9 |
| HPC (2) | hydroxypropyl cellulose NISSO HPC-SL (manufactured by Nippon Soda Co., Ltd.) | 30,000 to 50,000 | 84 to 140 | 3.0 to 5.9 |
| HPC (3) | hydroxypropyl cellulose NISSO HPC-L (manufactured by Nippon Soda Co., Ltd.) | 55,000 to 70,000 | 154 to 196 | 6.0 to 10.0 |
| HPC (4) | hydroxypropyl cellulose NISSO HPC-M (manufactured by Nippon Soda Co., Ltd.) | 110,000 to 150,000 | 308 to 420 | 150 to 400 |
| HPC (5) | hydroxypropyl cellulose NISSO HPC-H (manufactured by Nippon Soda Co., Ltd.) | 250,000 to 400,000 | 700 to 1,120 | 1,000 to 4,000 |

<Cellulose Derivatives>

TABLE 2

| Abbreviations in Tables | | 2% viscosity (mPa · s) |
| --- | --- | --- |
| CMC | carboxymethyl cellulose CMC Daicel 1190 (manufactured by Daicel Chemical Industries, Ltd.) | 1300 to 2,000 (1%) |
| HPMC | hydroxypropyl methyl cellulose METOLOSE 60SH (manufactured by Shin-Estu Chemical Co. Ltd.) | 50 |
| MC | methyl cellulose METOLOSE SM (manufactured by Shin-Estu Chemical Co. Ltd.) | 100 |

<Organic Solvents>
MeOH: methanol, saturated vapor pressure at 25° C.: 127 mmHg acetone, saturated vapor pressure at 25° C.: 231 mmHg ethyl acetate, saturated vapor pressure at 25° C.: 95 mmHg
MEK: methyl ethyl ketone, saturated vapor pressure at 25° C.: 91 mmHg trifluoroethanol, saturated vapor pressure at 25° C.: 75 mmHg
EtOH: ethanol, saturated vapor pressure at 25° C.: 59 mmHg trichloroethylene, saturated vapor pressure at 25° C.: 47 mmHg 1-buthanol, saturated vapor pressure at 25° C.: 6.8 mmHg <Fungicidal Test>

A suspension of spores of *Botrytis cinerea* as a fungicide-resistant fungus (107 spores/ml) was sprayed to cucumber seedlings (3 true leaves in development) at a rate of 10 ml per pot. Subsequently, each pot was left to stand still at a 90% relative humidity at 25° C.

Thereafter, agrichemical-containing compositions were each produced by mixing with 1 L of water 0.5 g of a Benlate wettable powder (content of benomyl as the active ingredient: 50 wt %, commercial product, fungicide), as well as hydroxypropyl cellulose (shown in the table as (A) cellulose derivative) and (C) an organic solvent in amounts as shown in Table 3. Each agrichemical-containing composition was sprayed at a rate of 5 ml per pot. Afterwards, each pot was left to stand still at a 85% relative humidity at 25° C., and the number of specks was counted. A preventive value relative to an untreated area was determined by calculation from the following formula. The higher the preventive value, the higher the agrichemical efficacy is.

Preventive value=(1−(Number of specks in treated area/Number of specks in untreated area))×100 [FORMULA 1]

An adhesion amount was quantified by extracting the active ingredient from each cucumber seedling subjected to the spraying in the same manner as in the fungicidal test. An adhesion amount relative value was determined by calculation from the following formula. The higher the adhesion amount relative value, the larger the amount of the agrichemical adhered to the target plant is. Specifically, after treating cucumber seedlings with the test solutions, the overground part of each cucumber seedling was cut off and quantified. Then, acetonitrile was applied to the overground part to extract Benlate adhered to the surface. After being dried and hardened, the extracted Benlate was dissolved in a certain amount of methanol, thus obtaining samples. The samples were quantitatively analyzed under the following conditions.

<Analyzing equipment: gas chromatography/mass spectrometer>
Analyzing Conditions
[Gas Chromatography (GC)]
Column used: 5% phenyl methyl silicon chemically bonded capillary column (inner diameter: 0.25 mm, length: 30 m, water phase thickness: 0.25 μm)
Column Temperature: 50° C. (1 min)-20° C./min-200° C.-5° C./min-280° C. (5 min)
Inlet Temperature: 250° C.
Carrier gas: helium
[Mass spectrometer (MS)]
Ionization energy: 70 eV
Measurement m/z: 146, 205

Adhesion amount relative value=((Amount of agrichemical detected from cucumber to which each test solution was sprayed)/(Amount of agrichemical detected from cucumber to which agrichemical was sprayed solely)×100 [FORMULA 2]

TABLE 3

| | Cellulose derivative (A) | Amount of (A) (g) | Organic solvent (C) | Amount of (C) (g) | Amount of (A)/ Amount of (C) | Content (%) when composition as whole is taken as 100 wt % | | | Preventive value (%) | Adhesion amount relative value |
| | | | | | | Water *1 | Organic solvent | Agri-chemical | Benlate wettable powder | Benlate wettable powder |
|---|---|---|---|---|---|---|---|---|---|---|
| Ex. 1 | HPC (1) | 0.5 | MEK | 0.25 | 2 | 99.88 | 0.02 | 0.05 | 80 | 209 |
| Ex. 2 | HPC (1) | 0.5 | MEK | 1.0 | 0.5 | 99.8 | 0.10 | 0.05 | 87 | 222 |
| Ex. 3 | HPC (1) | 0.5 | MEK | 5.0 | 0.1 | 99.4 | 0.50 | 0.05 | 82 | 211 |
| Ex. 4 | HPC (1) | 0.5 | MEK | 2.0 | 0.25 | 99.7 | 0.20 | 0.05 | 83 | 206 |
| Ex. 5 | HPC (1) | 1.0 | MEK | 0.5 | 2 | 99.8 | 0.05 | 0.05 | 81 | 200 |
| Ex. 6 | HPC (1) | 0.5 | MEK | 0.3 | 1.7 | 99.87 | 0.03 | 0.05 | 84 | 203 |
| Ex. 7 | HPC (1) | 1.0 | MEK | 1.0 | 1 | 99.75 | 0.10 | 0.05 | 87 | 220 |
| Ex. 8 | HPC (1) | 1.0 | MEK | 10 | 0.1 | 98.86 | 0.99 | 0.05 | 83 | 209 |
| Ex. 9 | HPC (1) | 1.0 | EtOH | 0.5 | 2 | 99.8 | 0.05 | 0.05 | 80 | 200 |
| Ex. 10 | HPC (1) | 0.5 | EtOH | 0.3 | 1.7 | 99.87 | 0.03 | 0.05 | 83 | 201 |
| Ex. 11 | HPC (1) | 1.0 | EtOH | 1.0 | 1 | 99.75 | 0.10 | 0.05 | 85 | 212 |
| Ex. 12 | HPC (1) | 1.0 | EtOH | 10 | 0.1 | 98.86 | 0.99 | 0.05 | 82 | 210 |
| Ex. 13 | HPC (1) | 5.0 | MEK | 2.5 | 2 | 99.21 | 0.25 | 0.05 | 83 | 208 |
| Ex. 14 | HPC (2) | 0.5 | MEK | 5.0 | 0.1 | 99.4 | 0.50 | 0.05 | 80 | 201 |
| Ex. 15 | HPC (3) | 0.5 | MEK | 5.0 | 0.1 | 99.4 | 0.50 | 0.05 | 81 | 201 |
| Ex. 16 | HPC (4) | 0.5 | MEK | 5.0 | 0.1 | 99.4 | 0.50 | 0.05 | 81 | 200 |
| Ex. 17 | HPC (5) | 0.5 | MEK | 5.0 | 0.1 | 99.4 | 0.50 | 0.05 | 82 | 201 |
| Comp. Ex. 1 | HPC (1) | 5.0 | MEK | 1.0 | 5 | 99.35 | 0.10 | 0.05 | 54 | 110 |
| Comp. Ex. 2 | HPC (1) | 0.5 | MEK | 0.2 | 2.5 | 99.88 | 0.02 | 0.05 | 68 | 111 |
| Comp. Ex. 3 | HPC (1) | 0.5 | MEK | 25 | 0.02 | 97.47 | 2.44 | 0.05 | 69 | 108 |
| Comp. Ex. 4 | HPC (1) | 0.1 | MEK | 10 | 0.01 | 98.95 | 0.99 | 0.05 | 53 | 105 |
| Untreated | — | — | — | — | — | — | — | — | 0 | — |

*1 Amount of water contained in Benlate wettable powder was regarded as 0 when making calculations.

As can be seen from the results in Table 3, the amount of the agrichemical adhered improved significantly. Thus, it was confirmed that the agrichemical-containing composition of the present invention improved the fungicide effect.

<Insecticidal Test>

Three rice seedlings were planted, 10 third instar leafhopper were grown per rice seedling and the efficacy of insecticides was tested by a dipping method. Agrichemical-containing compositions were each produced by mixing with 1 L of water 0.3 g of a Sumithion emulsion (content of MEP as the active ingredient: 50 wt %, commercial product, insecticide) and 0.3 g of a Trebon emulsion (content of ethofenprox as the active ingredient: 20 wt %, commercial product, insecticide) as well as hydroxypropyl cellulose (shown in the table as (A) cellulose derivative) and (C) an organic solvent in amounts as shown in Table 4. An insecticidal rate was determined by calculation from the following formula. The larger the insecticidal rate, the higher the agrichemical efficacy is.

Insecticidal rate (%)=(Number of insects alive in untreated area/Number of insects alive in treated area)/Number of insects alive in untreated area×100 [FORMULA 3]

An adhesion amount was quantified by extracting the active ingredients from leafhoppers subjected to the same treatment as in the insecticidal test. An adhesion amount relative value was determined by calculation from the following formula. The higher the adhesion amount relative value, the larger the amount of the agrichemicals adhered to the target insect pests is. Specifically, the quantification was performed as follows.

Quantification of Sumithion:

After treating leafhoppers with the test solutions, acetone was applied to the leafhoppers to extract Sumitihion adhered to the surface. After being dried and hardened, the extracted Sumitihion was dissolved in a certain amount of methanol, thus obtaining samples. The samples were quantitatively analyzed under the following conditions.

Analyzing equipment: high-performance liquid chromatography
Detector: ultraviolet spectrophotometer
Operation Conditions
Column filler: octadecylsilylated silica gel (particle size: 5 μm)
Column: 4.6 mm in inner diameter×150 mm in length
Column temperature: 40° C.
Detector: wavelength at 225 nm
Mobile phase: mixed solution of acetonitrile and water (acetonitrile:water=3:1)

Adhesion amount relative value=((Amount of agrichemical detected from leafhopper to which each test solution was sprayed)/(Amount of agrichemical detected from leafhopper to which agrichemical was sprayed solely)×100    [FORMULA 4]

TABLE 4

| | Cellulose derivative (A) | Amount of (A) (g) | Organic solvent (C) | Amount of (C) (g) | Amount of (A)/ Amount of (C) | Content (%) when composition as whole is taken as 100 wt % | | | Insecticidal rate (%) | | Adhesion amount relative value | |
|---|---|---|---|---|---|---|---|---|---|---|---|---|
| | | | | | | Water *2 | Organic solvent | Agri-chemical | Sumithion emulsion | Trebon emulsion | Sumithion emulsion | Trebon emulsion |
| Ex. 18 | HPC (1) | 0.5 | MEK | 0.25 | 2 | 99.90 | 0.02 | 0.03 | 80 | 81 | 201 | 203 |
| Ex. 19 | HPC (1) | 0.5 | MEK | 1.0 | 0.5 | 99.82 | 0.10 | 0.03 | 89 | 89 | 220 | 226 |
| Ex. 20 | HPC (1) | 0.5 | MEK | 5.0 | 0.1 | 99.42 | 0.50 | 0.03 | 81 | 82 | 202 | 206 |
| Ex. 21 | HPC (1) | 1.0 | MEK | 0.5 | 2 | 99.82 | 0.05 | 0.03 | 81 | 82 | 201 | 201 |
| Ex. 22 | HPC (1) | 1.0 | MEK | 1.0 | 1 | 99.77 | 0.10 | 0.03 | 87 | 86 | 214 | 220 |
| Ex. 23 | HPC (1) | 1.0 | MEK | 10 | 0.1 | 98.88 | 0.99 | 0.03 | 83 | 83 | 208 | 206 |
| Ex. 24 | HPC (1) | 5.0 | MEK | 2.5 | 2 | 99.23 | 0.25 | 0.03 | 81 | 82 | 206 | 201 |
| Ex. 25 | HPC (1) | 0.5 | MeOH | 1.0 | 0.5 | 99.82 | 0.10 | 0.03 | 90 | 91 | 226 | 229 |
| Ex. 26 | HPC (1) | 0.5 | EtOH | 1.0 | 0.5 | 99.82 | 0.10 | 0.03 | 92 | 91 | 231 | 240 |
| Ex. 27 | HPC (1) | 0.5 | ethyl acetate | 1.0 | 0.5 | 99.82 | 0.10 | 0.03 | 89 | 88 | 221 | 220 |
| Ex. 28 | HPC (1) | 0.5 | acetone | 1.0 | 0.5 | 99.82 | 0.10 | 0.03 | 92 | 93 | 229 | 239 |
| Ex. 29 | HPC (1) | 0.5 | trifluoro-ethanol | 1.0 | 0.5 | 99.82 | 0.10 | 0.03 | 83 | 81 | 209 | 204 |
| Ex. 30 | HPC (2) | 0.5 | MEK | 5.0 | 0.1 | 99.42 | 0.50 | 0.03 | 81 | 80 | 210 | 208 |
| Ex. 31 | HPC (3) | 0.5 | MEK | 5.0 | 0.1 | 99.42 | 0.50 | 0.03 | 82 | 82 | 212 | 210 |
| Ex. 32 | HPC (4) | 0.5 | MEK | 5.0 | 0.1 | 99.42 | 0.50 | 0.03 | 82 | 82 | 214 | 211 |
| Ex. 33 | HPC (5) | 0.5 | MEK | 5.0 | 0.1 | 99.42 | 0.50 | 0.03 | 81 | 82 | 210 | 208 |
| Comp. Ex. 5 | HPC (1) | 0.5 | trichloro-ethylene | 5.0 | 0.1 | 99.42 | 0.50 | 0.03 | 64 | 66 | 111 | 110 |
| Comp. Ex. 6 | HPC (1) | 0.5 | trichloro-ethylene | 5.0 | 1 | 99.42 | 0.50 | 0.03 | 62 | 64 | 110 | 109 |
| Comp. Ex. 7 | HPC (1) | 0.5 | trichloro-ethylene | 5.0 | 2 | 99.42 | 0.50 | 0.03 | 61 | 60 | 110 | 110 |
| Comp. Ex. 8 | HPC (1) | 0.5 | 1-buthanol | 5.0 | 0.1 | 99.42 | 0.50 | 0.03 | 60 | 60 | 120 | 105 |
| Comp. Ex. 9 | HPC (1) | 0.5 | 1-buthanol | 5.0 | 1 | 99.42 | 0.50 | 0.03 | 59 | 58 | 108 | 103 |
| Comp. Ex. 10 | HPC (1) | 0.5 | 1-buthanol | 5.0 | 2 | 99.42 | 0.50 | 0.03 | 58 | 57 | 109 | 102 |
| Comp. Ex. 11 | HPMC | 0.5 | MEK | 1.0 | 0.5 | 99.82 | 0.10 | 0.03 | 62 | 64 | 110 | 105 |

*2 Amount of water contained in Sumithion and Trebon emulsions was regarded as 0 when making calculations.

Analyzing equipment: gas chromatography/mass spectrometer
[Gas Chromatography (GC)]
Column used: 5% phenyl methyl silicon chemically bonded capillary column (inner diameter: 0.25 mm, length: 30 m, liquid phase thickness: 0.25 μm)
Column Temperature: 80° C. (2 min)-20° C./min-180° C.-5° C./min-240° C.-15° C./min-280° C. (5 min)
Inlet Temperature: 200° C.
Carrier gas: helium
[Mass spectrometer (MS)]
Ionization energy: 70 eV
Measurement m/z: 277, 260
Quantification of Trebon:
After treating leafhoppers with the test solutions, acetone was applied to the leafhoppers to extract Trebon adhered to the surface. After being dried and hardened, the extracted Trebon was dissolved in a certain amount of methanol, thus obtaining samples. The samples were quantitatively analyzed under the following conditions.

As can be seen from the results in Table 4, the amount of the agrichemicals adhered improved significantly. Thus, it was confirmed that the agrichemical-containing composition of the present invention improved the insecticidal effect.

[Miticidal Test]

Agrichemical-containing compositions were each produced by mixing with 1 L of water 0.3 g of a Nissoran wettable powder (content of hexythiazox as the active ingredient: 10 wt %) and 0.3 g of an Osadan wettable powder 25 (content of fenbutatin oxide as the active ingredient: 25 wt %) as well as hydroxypropyl cellulose (shown in the table as (A) cellulose derivative) and (C) an organic solvent in amounts as shown in Table 5. After planting adult female Kanzawa spider mites on kidney bean leaf disks at a rate of 30 mites per area by 3 repetitions, the mites were incubated at 25° C. for 24 hours. Subsequently, the leaf disks were immersed entirely in the test solutions for 5 seconds. Then, the leaf disks were taken out from the test solutions and set aside at 25° C. for 48 hours. Thereafter, the leaf disks were observed. A miticidal rate relative to an untreated case was determined by calculation from the following formula. The higher the miticidal rate, the higher the agrichemical efficacy is.

Miticidal rate (%)=(Number of mites alive in untreated area−Number of mites alive in treated area)/Number of mites alive in untreated area× 100   [FORMULA 5]

An adhesion amount was quantified by extracting the active ingredients from mites subjected to the same treatment as in the insecticidal test. An adhesion amount relative value was determined by calculation from the following formula. The higher the adhesion amount relative value, the larger the amount of the agrichemical adhered to the target insect pests is. Specifically, the quantification was performed as follows.

Quantification of Nissoran

After treating Kanzawa spider mites with the test solutions, acetonitril was applied to the mites to extract Nissoran. After being dried and hardened, the extracted Nissoran was dissolved in a certain amount of methanol, thus obtaining samples. The samples were quantitatively analyzed under the following conditions.

Analyzing equipment: high-performance liquid chromatography
Detector: ultraviolet spectrophotometer
Operation Conditions
Column filler: octadecylsilylated silica gel (particle size: 5 μm)
Column: 4 mm in inner diameter×150 mm in length
Column temperature: 40° C.
Detector: wavelength at 235 nm
Mobile phase: mixed solution of acetonitrile and water (acetonitrile:water=7:3)

Quantification of Osadan

After treating Kanzawa spider mites with the test solutions, acetonitril was applied to the mites to extract Osadan. After being dried and hardened, the extracted Osadan was dissolved in a certain amount of methanol, thus obtaining samples. The samples were quantitatively analyzed under the following conditions.

Analyzing equipment: gas chromatography
Detector: flame photometric detector (wavelength at 610 nm)
Operation Conditions
Column: 0.32 mm in inner diameter×30 m in length
Column filler: phenyl-methyl silicon
Column temperature: 120° C. (2 min)-10° C./min-200° C.-20° C./min-300° C. (5 min)
Test solution inlet temperature: 280° C.
Detector: 300° C.
Carrier gas: helium Adhesion amount relative value=((Amount of agrichemical detected from mite to which each test solution was sprayed)/(Amount of agrichemical detected from mite to which agrichemical was sprayed solely)×100   [FORMULA 6]

TABLE 5

| | Cellulose derivative (A) | Amount of (A) (g) | Organic solvent (C) | Amount of (C) (g) | Amount of (A)/ Amount of (C) | Content (%) when composition as whole is taken as 100 wt % | | | Miticidal rate (%) | | Adhesion amount relative value | |
|---|---|---|---|---|---|---|---|---|---|---|---|---|
| | | | | | | Water *3 | Organic solvent | Agri-chemical | Nissoran wettable powder | Osadan Wettable powder 25 | Nissoran wettable powder | Osadan Wettable powder 25 |
| Ex. 34 | HPC (1) | 0.5 | MEK | 0.25 | 2 | 99.90 | 0.02 | 0.03 | 82 | 81 | 202 | 204 |
| Ex. 35 | HPC (1) | 0.5 | MEK | 1.0 | 0.5 | 99.82 | 0.10 | 0.03 | 90 | 88 | 238 | 206 |
| Ex. 36 | HPC (1) | 0.5 | MEK | 5.0 | 0.1 | 99.42 | 0.50 | 0.03 | 81 | 82 | 206 | 206 |
| Ex. 37 | HPC (1) | 1.0 | MEK | 0.5 | 2 | 99.82 | 0.05 | 0.03 | 83 | 82 | 207 | 209 |
| Ex. 38 | HPC (1) | 1.0 | MEK | 1.0 | 1 | 99.77 | 0.10 | 0.03 | 90 | 89 | 224 | 231 |
| Ex. 39 | HPC (1) | 1.0 | MEK | 10 | 0.1 | 98.88 | 0.99 | 0.03 | 82 | 83 | 206 | 210 |
| Ex. 40 | HPC (1) | 5.0 | MEK | 2.5 | 2 | 99.23 | 0.25 | 0.03 | 83 | 82 | 209 | 208 |
| Ex. 41 | HPC (1) | 0.5 | MeOH | 1.0 | 0.5 | 99.82 | 0.10 | 0.03 | 92 | 91 | 221 | 229 |
| Ex. 42 | HPC (1) | 0.5 | ethyl acetate | 1.0 | 0.5 | 99.82 | 0.10 | 0.03 | 91 | 91 | 220 | 225 |
| Ex. 43 | HPC (2) | 0.5 | MEK | 5.0 | 0.1 | 99.42 | 0.50 | 0.03 | 82 | 80 | 225 | 231 |
| Ex. 44 | HPC (3) | 0.5 | MEK | 5.0 | 0.1 | 99.42 | 0.50 | 0.03 | 82 | 81 | 215 | 209 |
| Ex. 45 | HPC (4) | 0.5 | MEK | 5.0 | 0.1 | 99.42 | 0.50 | 0.03 | 81 | 81 | 219 | 211 |
| Ex. 46 | HPC (5) | 0.5 | MEK | 5.0 | 0.1 | 99.42 | 0.50 | 0.03 | 80 | 82 | 207 | 211 |
| Comp. Ex. 13 | CMC | 0.5 | MEK | 5.0 | 0.1 | 99.42 | 0.50 | 0.03 | 63 | 62 | 207 | 211 |
| Comp. Ex. 14 | CMC | 0.5 | MEK | 1.0 | 0.5 | 99.82 | 0.10 | 0.03 | 64 | 63 | 106 | 111 |
| Comp. Ex. 15 | CMC | 1.0 | MEK | 1.0 | 1 | 99.77 | 0.10 | 0.03 | 63 | 63 | 110 | 113 |
| Comp. Ex. 16 | HPC (1) | 0.1 | MEK | 10 | 0.01 | 98.97 | 0.99 | 0.03 | 62 | 63 | 110 | 111 |
| Comp. Ex. 17 | HPC (1) | 0.5 | MEK | 0.2 | 2.5 | 99.90 | 0.02 | 0.03 | 64 | 63 | 108 | 109 |
| Comp. Ex. 18 | HPC (1) | 10 | MEK | 100 | 0.1 | 90.07 | 9.01 | 0.03 | 49 | 50 | 106 | 108 |
| Comp. Ex. 19 | HPC (1) | 100 | MEK | 100 | 1 | 83.31 | 8.33 | 0.03 | 49 | 49 | 104 | 106 |
| Untreated | — | — | — | — | — | — | — | — | 0 | 0 | — | — |

*3 Amount of water contained in Nissoran wettable poweder and Osadan wettable powder 25 was regarded as 0 when making calculations.

As can be seen from the results in Table 5, it was confirmed that the agrichemical-containing composition of the present invention improved the miticidal effect.

[Herbicidal Test]

Pangola grass was germinated in pots. In order to increase the evenness among the pots, those in which pangola grass grew abnormally were discarded. The pots in which pangola grass grew to about 18 cm in height were used in the test. 10 g of a Touchdown solution (content of glyphosate trimesium salt as the active ingredient: 38 wt %, commercial product) and 3.7 g of a Roundup solution (content of glyphosate isopropyl amine salt as the active ingredient: 41 wt %, commercial product) were added to 1 L of water and hydroxypropyl cellulose (shown in the table as (A) cellulose derivative) and (C) an organic solvent in amounts as shown in Table 6 were further mixed to produce agrichemcial-containing compositions. Each test solution was sprayed to the pangola grass such that the solution was applied to the entire glass to evaluate the herbicidal effect. The herbicidal effect was evaluated as follows. The weight of the overground part of the pangola grass was measured after 14 days from the spraying of the solution, and a herbicidal rate relative to the weight of the overground part in an untreated area was determined by calculation from the following formula. The higher the herbicidal rate, the higher the agrichemical efficacy is.

Herbicidal rate (%)=(Weight of overground part in untreated area−Weight of overground part in treated area)/Weight of overground part in untreated area×100　　　[FORMULA 7]

An adhesion amount was quantified by extracting the active ingredients from pangola grass subjected to the same treatment as in the insecticidal test. An adhesion amount relative value was determined by calculation from the following formula. The higher the adhesion amount relative value, the larger the amount of the agrichemical adhered to the target plant is. Specifically, the quantification was performed as follows.

Quantification of Roundup and Touchdown:

After treating pangola grass with the test solutions, distilled water was applied to the pangola grass to extract Roundup or Touchdown adhered to the pangola grass. After being dried and hardened, the extracted Roundup or Touchdown was dissolved in a certain amount of distilled water, thus obtaining samples. The samples were quantitatively analyzed under the following conditions.

Analyzing equipment: high-performance liquid chromatography
Detector: equipped with fluorescence detector
Operation Conditions
Column filler: strong-base anion exchange resin (particle size: 10 μm)
Column: 4.5 mm in inner diameter×250 mm in length
Column temperature: 40° C.
Detector: excitation wavelength at 254 nm, fluorescence wavelength at 315 nm
Mobile phase: mixed solution of acetonitrile and 0.1 mol/L phosphoric acid-potassium solution (acetonitrile:phosphoric acid-potassium solution=1:3)

Adhesion amount relative value=((Amount of agrichemical detected from pangola grass to which each test solution was sprayed)/(Amount of agrichemical detected from pangola grass to which agrichemical was sprayed solely)×100　　　[FORMULA 8]

TABLE 6

| | Cellulose derivative (A) | Amount of (A) (g) | Organic solvent (C) | Amount of (C) (g) | Amount of (A)/ Amount of (C) | Water *[4] Touchdown solution | Water *[4] Roundup solution | Organic solvent Touchdown solution | Organic solvent Roundup solution |
|---|---|---|---|---|---|---|---|---|---|
| Ex. 47 | HPC (1) | 0.5 | MEK | 0.25 | 2 | 98.94 | 99.56 | 0.02 | 0.02 |
| Ex. 48 | HPC (1) | 0.5 | MEK | 1.0 | 0.5 | 98.86 | 99.48 | 0.10 | 0.10 |
| Ex. 49 | HPC (1) | 0.5 | MEK | 5.0 | 0.1 | 98.47 | 99.09 | 0.49 | 0.50 |
| Ex. 50 | HPC (1) | 1.0 | MEK | 0.5 | 2 | 98.86 | 99.48 | 0.05 | 0.05 |
| Ex. 51 | HPC (1) | 1.0 | MEK | 1.0 | 1 | 98.81 | 99.43 | 0.10 | 0.10 |
| Ex. 52 | HPC (1) | 1.0 | MEK | 10 | 0.1 | 97.94 | 98.55 | 0.98 | 0.99 |
| Ex. 53 | HPC (1) | 5.0 | MEK | 2.5 | 2 | 98.28 | 98.89 | 0.25 | 0.25 |
| Ex. 54 | HPC (1) | 0.5 | MeOH | 1.0 | 0.5 | 98.86 | 99.48 | 0.10 | 0.10 |
| Ex. 55 | HPC (1) | 0.5 | EtOH | 1.0 | 0.5 | 98.86 | 99.48 | 0.10 | 0.10 |
| Ex. 56 | HPC (2) | 0.5 | MEK | 5.0 | 0.1 | 98.86 | 99.48 | 0.49 | 0.50 |
| Ex. 57 | HPC (3) | 0.5 | MEK | 5.0 | 0.1 | 98.47 | 99.09 | 0.49 | 0.50 |
| Ex. 58 | HPC (4) | 0.5 | MEK | 5.0 | 0.1 | 98.47 | 99.09 | 0.49 | 0.50 |
| Ex. 59 | HPC (5) | 0.5 | MEK | 5.0 | 0.1 | 98.47 | 99.09 | 0.49 | 0.50 |
| Comp. Ex. 16 | CMC | 0.5 | MEK | 0.25 | 2 | 98.94 | 99.56 | 0.02 | 0.02 |
| Comp. Ex. 17 | CMC | 0.5 | MEK | 1.0 | 0.5 | 98.86 | 99.48 | 0.10 | 0.10 |
| Comp. Ex. 18 | CMC | 0.5 | MEK | 5.0 | 0.1 | 98.47 | 99.09 | 0.49 | 0.50 |
| Comp. Ex. 19 | MC | 0.5 | MEK | 1.0 | 0.5 | 98.86 | 99.48 | 0.10 | 0.05 |
| Comp. Ex. 20 | HPMC | 0.5 | MEK | 1.0 | 0.5 | 98.86 | 99.48 | 0.10 | 0.10 |
| Comp. Ex. 21 | HPC (1) | 0.5 | trichloroethylene | 5.0 | 0.1 | 98.47 | 99.09 | 0.49 | 0.99 |
| Comp. Ex. 22 | HPC (1) | 0.5 | trichloroethylene | 1.0 | 0.5 | 98.86 | 99.48 | 0.10 | 0.25 |
| Comp. Ex. 23 | HPC (1) | 0.5 | trichloroethylene | 0.5 | 1 | 98.91 | 99.53 | 0.05 | 0.10 |
| Comp. Ex. 24 | HPC (1) | 0.5 | MEK | 0.1 | 5.0 | 98.95 | 99.57 | 0.01 | 0.10 |
| Comp. Ex. 25 | HPC (1) | 0.5 | MEK | 0.2 | 2.5 | 98.94 | 99.56 | 0.02 | 0.50 |
| Comp. Ex. 26 | HPC (1) | 0.5 | MEK | 25 | 0.02 | 96.57 | 97.16 | 2.42 | 0.50 |
| Untreated | — | — | — | — | — | — | — | — | — |

| | Agrichemical Touchdown solution | Agrichemical Roundup solution | Herbicidal rate (%) Touchdown solution | Herbicidal rate (%) Roundup solution | Adhesion amount relative value Touchdown solution | Adhesion amount relative value Roundup solution |
|---|---|---|---|---|---|---|
| Ex. 47 | 0.99 | 0.37 | 82 | 81 | 209 | 211 |
| Ex. 48 | 0.99 | 0.37 | 90 | 91 | 233 | 222 |
| Ex. 49 | 0.98 | 0.37 | 83 | 82 | 206 | 218 |
| Ex. 50 | 0.99 | 0.37 | 83 | 84 | 209 | 214 |
| Ex. 51 | 0.99 | 0.37 | 91 | 92 | 234 | 223 |

TABLE 6-continued

| | | | | | | |
|---|---|---|---|---|---|---|
| Ex. 52 | 0.98 | 0.36 | 83 | 83 | 211 | 211 |
| Ex. 53 | 0.98 | 0.37 | 83 | 84 | 210 | 209 |
| Ex. 54 | 0.99 | 0.37 | 91 | 93 | 229 | 213 |
| Ex. 55 | 0.99 | 0.37 | 90 | 92 | 230 | 223 |
| Ex. 56 | 0.98 | 0.37 | 83 | 82 | 208 | 211 |
| Ex. 57 | 0.98 | 0.37 | 84 | 85 | 209 | 209 |
| Ex. 58 | 0.98 | 0.37 | 84 | 83 | 210 | 204 |
| Ex. 59 | 0.98 | 0.37 | 85 | 84 | 216 | 206 |
| Comp. Ex. 16 | 0.99 | 0.37 | 61 | 62 | 114 | 115 |
| Comp. Ex. 17 | 0.99 | 0.37 | 63 | 63 | 115 | 116 |
| Comp. Ex. 18 | 0.98 | 0.37 | 62 | 62 | 116 | 111 |
| Comp. Ex. 19 | 0.99 | 0.37 | 64 | 63 | 110 | 116 |
| Comp. Ex. 20 | 0.99 | 0.37 | 61 | 62 | 110 | 110 |
| Comp. Ex. 21 | 0.98 | 0.36 | 58 | 59 | 108 | 109 |
| Comp. Ex. 22 | 0.98 | 0.37 | 54 | 58 | 104 | 110 |
| Comp. Ex. 23 | 0.99 | 0.37 | 58 | 57 | 110 | 104 |
| Comp. Ex. 24 | 0.99 | 0.37 | 60 | 60 | 112 | 110 |
| Comp. Ex. 25 | 0.98 | 0.37 | 69 | 68 | 120 | 109 |
| Comp. Ex. 26 | 0.98 | 0.37 | 69 | 69 | 121 | 109 |
| Untreated | | | 0 | 0 | — | — |

*[4] Amount of water contained in Touchdown solution and Roundup solution 25 was regarded as 0 when making calculations.

As can be seen from the results in Table 6, it was confirmed that the agrichemical-containing composition of the present invention improved the herbicidal effect.

INDUSTRIAL APPLICABILITY

The agrichemical-containing composition of the present invention is useful for, for example, a fungicide, a plant growth regulator, a miticide, and a herbicide.

The invention claimed is:

1. A method for enhancing efficacy of an agrichemical, comprising adding a composition comprising hydroxypropyl cellulose, an organic solvent having a saturated vapor pressure of 50 mmHg or higher at 25° C., and water to the agrichemical,
   wherein when a total of the composition and the agrichemical is taken as 100 wt %, a content of the organic solvent is 0.02 to 1 wt %,
   a weight ratio of the hydroxypropyl cellulose to the organic solvent (hydroxypropyl cellulose/organic solvent) is 0.1:1 to 2:1,
   a content of water is 95 wt % or more,
   the organic solvent is one or more selected from the group consisting of methanol, ethanol, acetone, methyl ethyl ketone, and ethyl acetate,
   the agrichemical is a fungicide, an insecticide or a miticide; and
   wherein the composition facilitates the formation of a film containing the agrichemical.

2. The method according to claim 1, wherein the hydroxypropyl cellulose is represented by the formula (I):

$$\left[ \begin{array}{c} \text{CH}_2\text{OR} \\ \text{H} \\ \text{OR} \\ \text{H} \\ \text{OR} \end{array} \right]_n \quad (I)$$

wherein R is H or —(CH$_2$CH(CH$_3$)—O)$_m$H wherein m is 0 or an integer of 1 to 5 and all of Rs in the formula (I) do not have m as 0 at the same time.

3. An agrichemical-containing composition comprising hydroxypropyl cellulose,
   an agrichemical,
   an organic solvent having a saturated vapor pressure of 50 mmHg or higher at 25° C., and
   water,
   wherein when the composition as whole is taken as 100 wt %, a content of the organic solvent is 0.02 to 1 wt %,
   a weight ratio of the hydroxypropyl cellulose to the organic solvent (hydroxypropyl cellulose/organic solvent) is 0.1:1 to 2:1,
   a content of water is 95 wt % or more,
   the organic solvent is one or more selected from the group consisting of methanol, ethanol, acetone, methyl ethyl ketone, and ethyl acetate,
   the agrichemical is a fungicide, an insecticide or a miticide; and
   wherein the composition facilitates the formation of a film containing the agrichemical.

4. The agrichemical-containing composition according to claim 3, wherein the hydroxypropyl cellulose is represented by the formula (I):

$$\left[ \begin{array}{c} \text{CH}_2\text{OR} \\ \text{H} \\ \text{OR} \\ \text{H} \\ \text{OR} \end{array} \right]_n \quad (I)$$

wherein R is H or —(CH$_2$CH(CH$_3$)—O)$_m$H wherein m is 0 or an integer of 1 to 5 and all of Rs in the formula (I) do not have m as 0 at the same time.

5. A method for improving quality of a plant, comprising applying the agrichemical-containing composition according to claim 3 to the plant.

* * * * *